US011904064B2

(12) United States Patent
Park et al.

(10) Patent No.: US 11,904,064 B2
(45) **Date of Patent: *Feb. 20, 2024**

(54) AUTOMATED DECONTAMINATION OF COMPLEX AREAS

(71) Applicant: The Boeing Company, Chicago, IL (US)

(72) Inventors: Shawn Hyunsoo Park, Huntsville, AL (US); Leora Peltz, Pasadena, CA (US); Andrew Gerhard Wallburg, Madison, AL (US)

(73) Assignee: The Boeing Company, Chicago, IL (US)

( * ) Notice: Subject to any disclaimer, the term of this patent is extended or adjusted under 35 U.S.C. 154(b) by 329 days.

This patent is subject to a terminal disclaimer.

(21) Appl. No.: 17/103,277

(22) Filed: Nov. 24, 2020

(65) Prior Publication Data

US 2021/0093740 A1 Apr. 1, 2021

Related U.S. Application Data

(60) Continuation of application No. 16/667,613, filed on Oct. 29, 2019, now Pat. No. 10,881,753, which is a (Continued)

(51) Int. Cl.

*A61L 2/22* (2006.01)
*A61L 9/14* (2006.01)
*A61L 2/00* (2006.01)

(52) U.S. Cl.

CPC *A61L 2/22* (2013.01); *A61L 2/00* (2013.01); *A61L 9/14* (2013.01); *A61L 2202/15* (2013.01);

(Continued)

(58) Field of Classification Search

CPC .................................... A61L 2/22; A61L 9/14
See application file for complete search history.

(56) References Cited

U.S. PATENT DOCUMENTS 6,206,300 B1 * 3/2001 Roudebush ........... B05B 7/2486 239/164
8,416,554 B2 4/2013 Peltz et al.

(Continued)

FOREIGN PATENT DOCUMENTS

AU 2018200617 A1 8/2018
CN 101972128 A 2/2011

(Continued)

OTHER PUBLICATIONS

English Translation of Document No. CN 104249032 A provided by the European Patent Office website espacenet.com: Jianping Lu; Spraying Equipment; Dec. 31, 2014 (Year: 2014).*

(Continued)

*Primary Examiner* — Kevin Joyner
(74) *Attorney, Agent, or Firm* — Kwan & Olynick LLP

(57) ABSTRACT

Provided are mobile decontamination units and methods of using such units for decontaminating various areas, such as aircraft cabins. A mobile decontamination unit comprises at least one aerosol dispersing nozzle and at least one aerosol directing fan. The nozzle disperses disinfectant in the aerosol form, while the fan directed this aerosol to surfaces being decontaminated. Aerosol dispersing parameters, such the nozzle and fan orientations, dispersing rate, fan speed, and the like, are determined based on area characteristics. Specifically, orientations of different surfaces, temperature, humidity and/or other like characteristics may be considered. Some characteristics may be obtained by the mobile decontamination unit after its deployment in the area, such as using its sensors. Other characteristics, such as area layout, may be preloaded to the mobile decontamination unit (Continued)

prior to its deployment. The dispersing parameters are determined to ensure through decontamination of the surfaces in the area.

20 Claims, 8 Drawing Sheets

Related U.S. Application Data division of application No. 15/417,994, filed on Jan. 27, 2017, now Pat. No. 10,507,256.

(52) U.S. Cl.
CPC ....... *A61L 2202/16* (2013.01); *A61L 2202/25* (2013.01)

(56) References Cited

U.S. PATENT DOCUMENTS

| | | | |
|---|---|---|---|
| 8,715,586 B2 | 5/2014 | Park et al. | |
| 8,936,944 B2 | 1/2015 | Peltz et al. | |
| 8,992,830 B2 | 3/2015 | Park et al. | |
| 10,507,256 B2 | 12/2019 | Park et al. | |
| 10,881,753 B2 | 1/2021 | Park et al. | |
| 2007/0098592 A1 | 5/2007 | Buczynski et al. | |
| 2008/0063561 A1 | 3/2008 | Hooser | |
| 2011/0091354 A1 | 4/2011 | Schwartz et al. | |
| 2011/0171065 A1 | 7/2011 | Park et al. | |
| 2014/0271347 A1 | 9/2014 | Park et al. | |
| 2015/0290348 A1* | 10/2015 | Taoka | A61L 2/14 250/491.1 |
| 2016/0033374 A1 | 2/2016 | Camp et al. | |
| 2017/0100497 A1 | 4/2017 | Zarfl | |
| 2018/0214591 A1 | 8/2018 | Park et al. | |
| 2020/0069828 A1 | 3/2020 | Park et al. | |

FOREIGN PATENT DOCUMENTS

| | | |
|---|---|---|
| CN | 203766592 U | 8/2014 |
| CN | 104044740 A | 9/2014 |
| CN | 104249032 A | 12/2014 |
| CN | 104740670 A | 7/2015 |
| CN | 204910199 U | 12/2015 |
| CN | 106139196 A | 11/2016 |
| CN | 106179818 A | 12/2016 |
| EP | 3354291 A1 | 8/2018 |
| JP | 2001009335 A | 1/2001 |
| JP | 2012120738 A | 6/2012 |
| WO | 2012032338 A1 | 3/2012 |

OTHER PUBLICATIONS

U.S. Appl. No. 16/667,613, Notice of Allowance and Fees Due (Ptol-85), dated Sep. 1, 2020, 5 pgs.
U.S. Appl. No. 16/667,613, Notice of Allowance and Fees Due (Ptol-85), dated Dec. 7, 2020, 5 pgs.
U.S. Appl. No. 16/667,613, Notice of Allowance and Fees Due (Ptol-85), dated Aug. 26, 2020, 8 pgs.
U.S. Appl. No. 15/417,994, Examiner Interview Summary dated Jul. 16, 2019, 4 pgs.
U.S. Appl. No. 15/417,994, Non Final Office Action dated May 14, 2019, 12 pgs.
U.S. Appl. No. 15/417,994, Notice of Allowance dated Jul. 30, 2019, 9 pgs.
U.S. Appl. No. 15/417,994, Restriction Requirement dated Mar. 1, 2019, 7 pgs.
Chinese Application Serial No. 201810071216.5, Office Action dated Sep. 24, 2020, 29 pgs.
European Application Serial No. 18153197.1, Office Action dated Jun. 1, 2018, 12 pgs.
Netherlands Application Serial No. 2018402, Search Report and Written Opinion dated Nov. 9, 2017, 18 pgs.
Park, Shawn Hyunsoo., et al., Automated Decontamination of Complex Areas, 37 pgs.
Brazilian Application No. 102018001692-0, Office action dated Apr. 14, 2022, 7 pgs.
Canadian Application Serial No. 2,992,202, Office Action dated Mar. 18, 2021, 4 pgs.
Mexican Application Serial No. MX/a/2018/001031, Office Action dated Feb. 18, 2021, 6 pgs.
European Application Serial No. 18153197.1, Office Action dated Aug. 4, 2021, 4 pgs.
Notice of Reasons For Rejection for Japanese Application No. 2018-11300, dated Oct. 3, 2023, 7 pgs.

* cited by examiner

System 200
- Remote Unit(s) 210
  - HVAC Unit 212
- Tether 219
- Mobile Decontamination Unit 300
  - Base Portion 310
    - Head Positioning Module 314
    - Decontaminant Storage Module 314
      - Decontaminant 315
    - Power Module 318
    - Connector 319
    - Aerosol dispersing Nozzles 322
    - Mobility Module 312
  - Head Portion 320
    - Aerosol dispersing Nozzles 322
    - Aerosol Directing Fans 324
      - Fan Heaters 326
  - Sensor(s) 328
    - Biological Sensor 328a
    - Chemical Sensor 328b
    - Temperature Sensor 328c
    - Humidity Sensor 328d
    - Camera 328e
  - Unit Controller 302
  - Database 304
  - I/O Module 306
- Area 100
  - Area Characteristics 102
  - Surfaces 110

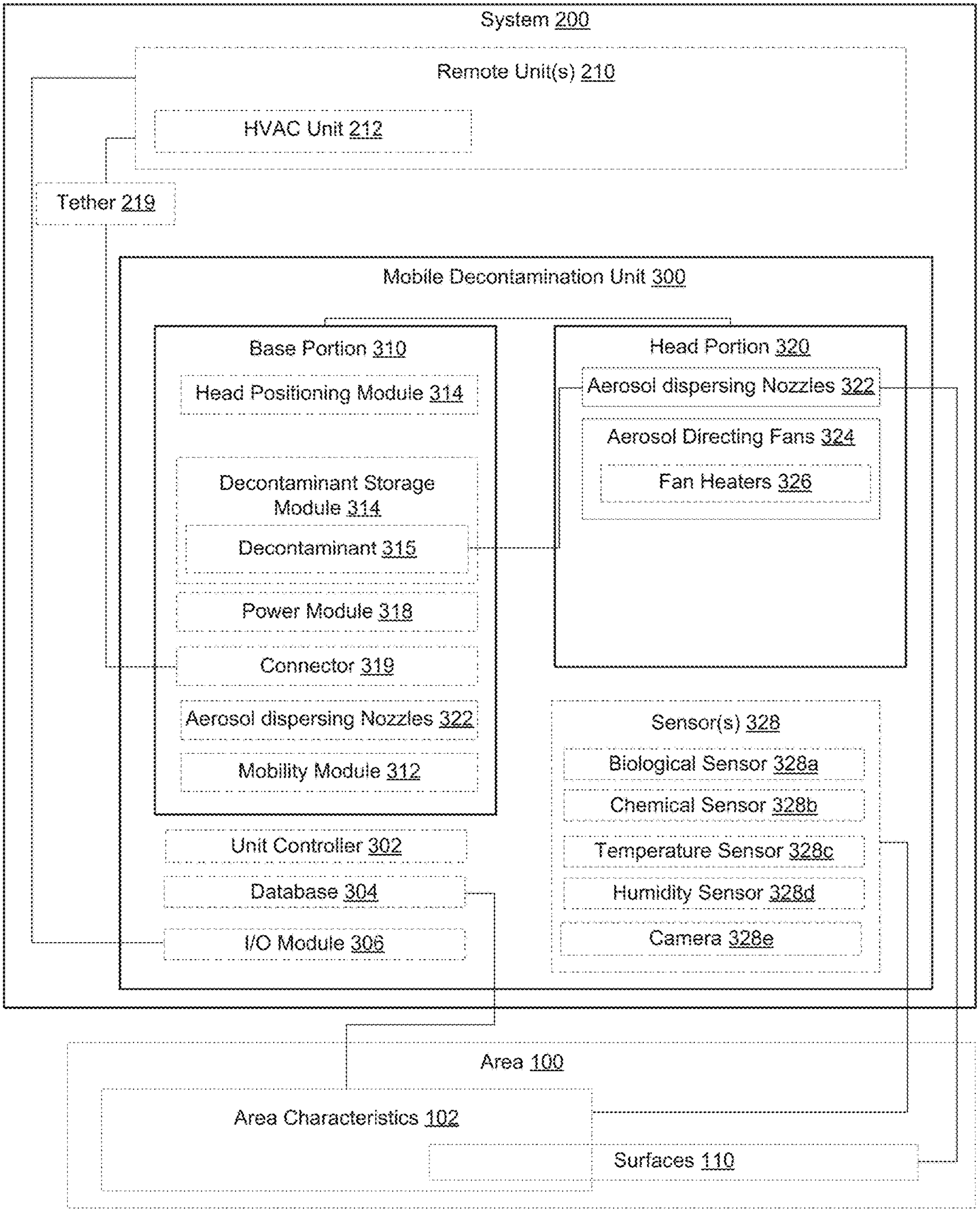

*FIG. 2A*

```
                          ┌─ Start ─┐
                          └────┬────┘
                               ▼
       ┌───────────────────────────────────────────────────┐
       │   Deploy Mobile Decontamination Unit in Area 410  │
       └───────────────────────┬───────────────────────────┘
                               ▼
       ┌───────────────────────────────────────────────────┐
       │      Determine Aerosol Dispersing Parameters 420  │
       │   ┌───────────────────────────────────────────┐   │
       │   │      Obtain Area Characteristics 422      │   │
       │   └───────────────────────────────────────────┘   │
       │   ┌───────────────────────────────────────────┐   │
       │   │      Change Area Characteristics 424      │   │
       │   │  ┌─────────────────────────────────────┐  │   │
       │   │  │  Operate One or More Area Systems 426│  │   │
       │   │  └─────────────────────────────────────┘  │   │
       │   └───────────────────────────────────────────┘   │
       └───────────────────────┬───────────────────────────┘
                               ▼
       ┌───────────────────────────────────────────────────┐
       │       Change Aerosol Dispersing Parameters 430    │
       └───────────────────────┬───────────────────────────┘
                               ▼
       ┌───────────────────────────────────────────────────┐
       │  Supply Material / Power to Mobile Decontamination Unit 435 │
       └───────────────────────┬───────────────────────────┘
                               ▼
       ┌───────────────────────────────────────────────────┐
       │         Disperse Decontaminant in Area 440        │
       └───────────────────────┬───────────────────────────┘
                               ▼
       ┌───────────────────────────────────────────────────┐
       │         Direct Decontaminant within Area 450      │
       └───────────────────────┬───────────────────────────┘
                               ▼
       ┌───────────────────────────────────────────────────┐
       │    Move Mobile Decontamination Unit within Area 460│
       └───────────────────────┬───────────────────────────┘
                               ▼
       ┌───────────────────────────────────────────────────┐
       │            Operate Stationary Unit(s) 470         │
       └───────────────────────┬───────────────────────────┘
                               ▼
                      ◇ Remaining Area? 480 ◇ ── YES ──▶ (to 424)
                               │
                              NO
                               ▼
                          ┌─ Done ─┐
                          └────────┘
```

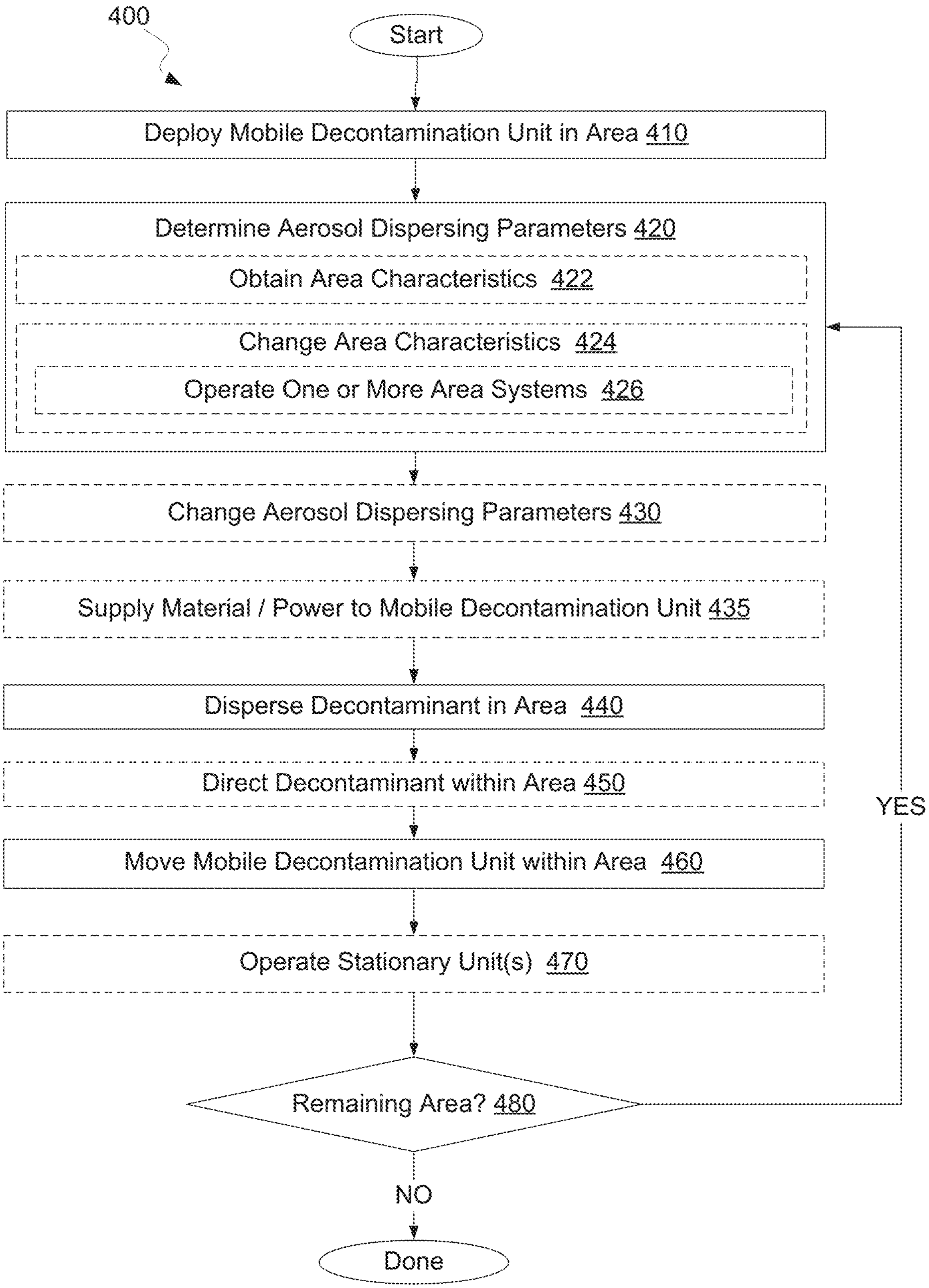

*FIG. 4*

AUTOMATED DECONTAMINATION OF COMPLEX AREAS

CROSS-REFERENCE TO RELATED APPLICATION

This application is a continuation of U.S. application Ser. No. 16/667,613, entitled "AUTOMATED DECONTAMINATION OF COMPLEX AREAS," filed on 29 Oct. 2019, which is a divisional of U.S. application Ser. No. 15/417,994, entitled "AUTOMATED DECONTAMINATION OF COMPLEX AREAS," filed on 27 Jan. 2017, issued as U.S. Pat. No. 10,507,256 on 17 Dec. 2019, both of which are incorporated herein by reference in their entirety for all purposes.

FIELD

This disclosure relates to decontamination of complex areas and, more specifically, to methods and systems of automated decontamination of areas having hard-to-access surfaces such as aircraft cabins.

BACKGROUND

Contaminants may be introduced or appear in various areas causing the areas to become unsuitable for further use. For example, with the growing popularity of air and other types of travel and new destinations, the potential for transmission of infectious diseases has dramatically increased. Some types and levels of contamination may be controlled by air filtration, as well as wiping exposed surfaces with disinfecting agents. However, these methods can be costly, time consuming, expose humans (e.g., cleaning personnel) to contaminants and/or decontaminants, and have other unintended results. For example, many modern aircraft have large cabins with many hard to access surfaces making it difficult to perform through decontamination during short landing periods. Many hidden surfaces and small cavities may remain unattended and can retain substantial amounts of contaminants. Furthermore, many biological pathogens are quite resilient at room temperatures and require concentrated harsh chemicals, such as peroxides and/or acids, which may be undesirable for some surfaces

SUMMARY

Provided are mobile decontamination units and methods of using such units for decontaminating various areas, such as aircraft cabins. A mobile decontamination unit comprises at least one aerosol dispersing nozzle and at least one aerosol directing fan. The nozzle disperses disinfectant in the aerosol form while the fan directs aerosol to surfaces being decontaminated. Aerosol dispersing parameters, such the nozzle and fan orientations, dispersing rate, fan speed, and the like, are determined based on area characteristics. Specifically, orientation of different surfaces, temperature, humidity and/or other like characteristics may be considered. Some characteristics may be obtained by the mobile decontamination unit after its deployment in the area, for example, using of its sensors. Other characteristics, such as area layout, may be preloaded into the mobile decontamination unit prior to its deployment. The dispersing parameters are determined to ensure through decontamination of the surfaces in the area.

In some examples, method for decontaminating an area comprises deploying a mobile decontamination unit in the area, determining aerosol dispersing parameters, dispersing a decontaminant in a form of decontaminant droplets, and directing the decontaminant droplets to surfaces in the area. The mobile decontamination unit comprises an aerosol dispersing nozzle and an aerosol directing fan. The aerosol dispersing nozzle is used for dispersing the decontaminant. Specifically, the decontaminant is dispersed in an aerosol form comprising the decontaminant droplets. Furthermore, the decontaminant is dispersed in accordance with the aerosol dispersing parameters, which are determined based on area characteristics. The aerosol directing fan is used to direct the decontaminant droplets to the surfaces.

In some examples, determining the aerosol dispersing parameters is further performed based on characteristics of the decontaminant, which may be referred to as decontaminant characteristics. These decontaminant characteristics may be used together with the area characteristics to determine the aerosol dispersing parameters. Some examples of the decontaminant characteristics include density, surface tension, composition, and the like.

In some examples, determining the aerosol dispersing parameters comprises obtaining the area characteristics. Some examples of these area characteristics include humidity of the area, temperature of the area, contaminant type, orientation of the surfaces, and the like. The area characteristics may be obtained using a sensor of the mobile decontamination unit. This location acquisition of the area characteristics allows using the mobile decontamination unit even when some information about the area is unknown. For example, the temperature of the area may be initially unknown or it may change during the decontamination process. The temperature may be monitored locally by the mobile decontamination unit or via a temperature sensor.

In some examples, the area characteristics are stored in a database of the mobile decontamination unit. For example, the database may be preloaded with a layout of the area, surface conditions, and/or expected environmental conditions (e.g., humidity, temperature). The area characteristics stored in the database may be combined with additional area characteristics obtained locally by the mobile decontamination unit. In some examples, some area characteristics and/or dispensing parameters may be transmitted to the mobile decontamination unit from an external unit, e.g., sensors provided in the area, external controllers, and the like. Likewise, the mobile decontamination unit may transmit some area characteristics and/or dispensing parameters to the external unit.

In some examples, the overall operation of determining the aerosol dispersing parameters involves changing at least some area characteristics prior to finalizing the dispersing parameters. For example, initially, some area characteristics may be suboptimal for effective decontamination, e.g., the temperature may be too low or too high. These area characteristics may be changed to a set range, e.g., the range acceptable decontamination. The operation of determining the aerosol dispersing parameters may not be complete until the area characteristics are changed and within the set range. Alternatively, initial aerosol dispersing parameters may be determined and the process may continue with dispersing the decontaminant while the area characteristics are changed. New aerosol dispersing parameters may be determined when the change to the area characteristics is complete.

In some examples, changing the area characteristics comprises operating a remote unit, which is external to the mobile decontamination unit. The mobile decontamination unit may send instructions to the remote unit to perform changes to the area characteristics. Some examples of the remote unit include a heating-ventilation-air conditioning (HVAC) unit, a humidifier, an ozone generator, and the like. The remote unit should be distinguished from components of the mobile decontamination unit that may also be operable to change the area characteristics. For example, the remote unit may be a heater, different from a heater coupled to the aerosol directing fan of the mobile decontamination unit.

In some examples, determining the aerosol dispersing parameters is performed using a unit controller of the mobile decontamination unit. In the same or other examples, determining the aerosol dispersing parameters is performed remotely (e.g., by a remote unit) and then transmitted to the mobile decontamination unit. For example, a remote unit may have its own controller. The initial set of the aerosol dispersing parameters may be transmitted to the mobile decontamination unit and, in some examples, further modified at the mobile decontamination unit, for example, based on locally obtained area characteristics.

In some examples, the method further comprises moving the mobile decontamination unit in the area. For example, the mobile decontamination unit may be moved to access other parts of the area thereby allowing decontamination of larger areas. Furthermore, the mobile decontamination unit may be moved within the area to change orientation of its aerosol dispersing nozzle and aerosol directing fan relative to the surfaces in the area. For example, the mobile decontamination unit may rotate to provide a more appropriate angle for dispersing and/or to more uniformly disperse the decontaminant.

In some examples, moving the mobile decontamination unit in the area is performed while dispersing the decontaminant. In other words, the moving operation may overlap with the decontaminant dispersing operation. This feature ensures continuity of the dispersing operation, enhances uniformity of the decontamination, and improves the speed of the overall process.

Furthermore, moving the mobile decontamination unit in the area may be performed automatically based on the area characteristics. For example, the mobile decontamination unit may include a mobility module that allows the mobile decontamination unit to move without external help (e.g., from an operator). This feature allows to avoid exposing humans to potential contaminants and/or decontaminants in the area.

In some examples, the method further comprises changing the aerosol dispersing parameters. This may involve changing one or more of the following parameters: the orientation of the aerosol dispersing nozzle relative to the area, the orientation of the aerosol directing fan relative to the area, the power of heaters, the fan speed, the dispensing rate, and the like. Such changes may be performed to accommodate changes in area characteristics from one part of the area to another. In some examples, the orientation of the aerosol dispersing nozzle may be changed while dispersing the decontaminant, e.g., while moving from one surface to another.

In some examples, changing the aerosol dispersing parameters comprises both changing the orientation of the aerosol dispersing nozzle and changing the orientation of the aerosol directing fan. The mobile decontamination unit may maintain a certain relationship between the orientation of the aerosol dispersing nozzle and that of the aerosol directing fan. For example, changing both the orientation of the aerosol dispersing nozzle and the orientation of the aerosol directing fan comprises changing orientation of a head portion of the mobile decontamination unit relative to a base portion of the mobile decontamination unit. The head portion comprises (and supports) the aerosol dispersing nozzle and the aerosol directing fan. In other words, when the head portion changes its orientation relative to the base portion, which would be also relative to the area, the orientation of the nozzle and fan relative the area changes too. In some examples, changing the orientation of the head portion relative to the base portion comprises raising the head portion relative to the base portion and/or rotating the head portion relative to the base portion. It should be noted that the base portion may also change its orientation relative to the area, e.g., by moving the mobile decontamination unit in the area. This change in the orientation of the base portion changes the orientation of the entire mobile decontamination unit and all of its components, including any nozzles and fans.

In some examples, directing the decontaminant droplets to the surfaces comprises forming a turbulent air flow around the decontaminant droplets. The turbulent air flow may be formed by the aerosol directing fan. In some examples, the turbulent air flow may be formed, at least in part, by the remote unit.

In some examples, dispersing the decontaminant within the area and directing the decontaminant droplets to the surfaces overlap in time. Specifically, the aerosol directing fan may be operational (e.g., at all times) while dispersing the decontaminant. The flow generated by the aerosol directing fan helps to direct the decontaminant droplets and to carry the decontaminant droplets longer distances than if no fans are used (e.g., dispersing the decontaminant droplets in quiescent air).

In some examples, determining the aerosol dispersing parameters comprises determining the orientation of the aerosol dispersing nozzle and/or the orientation of the aerosol directing fan based on the orientation of the surfaces in the area. This nozzle-fan-surface orientation relationship may be used to ensure that all surfaces get adequate amounts of the decontaminant.

In some examples, the method further comprises obtaining the orientation of the surfaces in the area. This operation may be performed using a camera of the mobile decontamination unit. Alternatively, or additionally, this information may be retrieved from a database of the mobile decontamination unit. In other words, the database may contain at least some area characteristics, which may be added to the database prior to deployment of the mobile decontamination unit in the area.

In some examples, the aerosol dispersing parameters comprises a temperature ramping profile of an air directed by the aerosol directing fan. The temperature ramping profile may be linear.

In some examples, the method further comprises supplying the decontaminant to the mobile decontamination unit while dispersing the decontaminant within the area. For example, the mobile decontamination unit may be tethered to a remote unit, which has a decontaminant storage. Eliminating an onboard storage and supplying the decontaminant externally allows to reduce the weight of the mobile decontamination unit. On the other hand, the mobile decontamination unit without any tethers and with an onboard decontaminant storage module may be more mobile in the area since tethers may restrict the range, orientations, and other movement characteristics of the mobile decontamination unit.

In some examples, the area decontaminated by the mobile decontamination unit is an aircraft cabin. Aircraft cabins are highly-populated enclosed areas that may be used for prolonged periods of time (e.g., long flights). Furthermore, aircraft cabins have many different surfaces made from different materials, making decontamination process particularly challenging.

Also provided is a mobile decontamination unit for decontaminating an area. The mobile decontamination unit comprises a base portion, a head portion, an aerosol dispersing nozzle, and an aerosol directing fan. The base portion comprises a mobility module operable to move the mobile decontamination unit around and at least within the area. The head portion may be movably coupled to the base portion. The aerosol dispersing nozzle may be operable to disperse a decontaminant within the area in an aerosol form comprising a decontaminant droplets. The aerosol directing fan may be operable to direct the decontaminant droplets of the decontaminant to surfaces in the area.

In some examples, the mobile decontamination unit further comprises a unit controller. The unit controller may be operable to determine aerosol dispersing parameters based on area characteristics. Furthermore, the unit controller may be operable to control operations of the aerosol dispersing nozzle, the aerosol directing fan, and the mobility module.

The mobile decontamination unit may further comprise a database, comprising at least a portion of the area characteristics. In other words, at least a portion of the area characteristics may be stored locally in the mobile decontamination unit. One example of such characteristics is area layout. Additional characteristics may be transmitted to the mobile decontamination unit and/or obtained by the mobile decontamination unit after being deployed in the area. For example, the mobile decontamination unit may further comprise a sensor selected from the group consisting of a biological sensor, a chemical sensor, a temperature sensor, a humidity sensor, and a camera. The sensor may be operable to obtain the area characteristics and transmit the area characteristics to the unit controller for further use, e.g., to determine the dispensing parameters.

In some examples, the mobility module is controllable by the unit controller based on the area characteristics obtained from the area. For example, the unit controller may choose to change the position of the mobile decontamination unit in the area and control the mobility module to implement these changes.

In some examples, the aerosol dispersing nozzle and the aerosol directing fan are movable at least with respect to the base portion. For example, the aerosol dispersing nozzle and the aerosol directing fan may positioned on a head portion, which may be raisable and/or rotatable relative to the base portion. Furthermore, the aerosol dispersing nozzle and the aerosol directing fan may change their orientation relative to the head portion.

In some examples, the aerosol dispersing nozzle and the aerosol directing fan are pivotable (or tiltable) relative to the center axis of the mobile decontamination unit. The aerosol dispersing nozzle and the aerosol directing fan may be rotatable around the center axis of the mobile decontamination unit.

In some examples, the mobile decontamination unit further comprises a connector for connecting a tether selected from the group consisting of an electrical power line, a pneumatic line, a communication line, and a decontaminant supply line. The mobile decontamination unit may comprise a decontaminant storage module. The mobile decontamination unit may further comprise a communication module for communicating with a system of the area.

The features and functions that have been discussed can be achieved independently in various examples or may be combined in yet other examples further details of which can be seen with reference to the following description and drawings.

BRIEF DESCRIPTION OF THE DRAWINGS

FIG. 2A is a schematic block diagram of a mobile decontamination unit as part of a system, in accordance with some examples.

FIG. 4 is a process flowchart corresponding to a method for decontaminating of an area, in accordance with some examples.

DETAILED DESCRIPTION

Figure 1A:
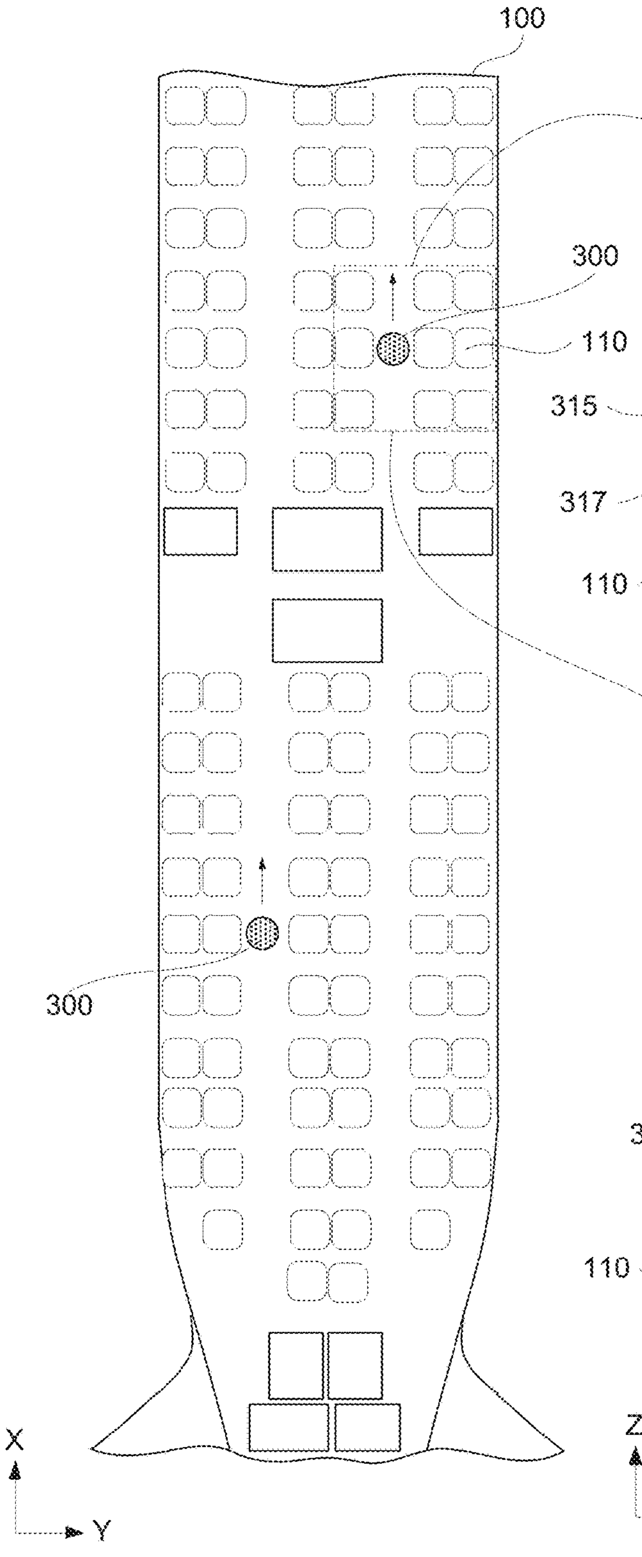
FIGS. 1A-1D are schematic representations of a mobile decontamination unit deployed within an area (represented as an aircraft cabin), in accordance with some examples.

In the following description, numerous specific details are set forth in order to provide a thorough understanding of the presented concepts. The presented concepts may be practiced without some or all of these specific details. In other instances, well known process operations have not been described in detail so as to not unnecessarily obscure the described concepts. While some concepts will be described in conjunction with the specific examples, it will be understood that these examples are not intended to be limiting.

Introduction

Decontamination of complex areas can be challenging and often cannot be performed by human operators because of the required speed and/or exposure to contaminants and decontaminants. Provided are automated mobile decontamination units and methods of using such units for decontaminating various areas, especially complex areas, such as aircraft cabins. A mobile decontamination unit may include nozzles (or injectors) to disperse a decontaminant in aerosol form, forming a cloud of decontaminant droplets. The cloud assumes a “plume shape”, which may be a fixed characteristic of the nozzle, and also a function of some dispersing parameters, such as the decontaminant pressure and the flow rate. The “plume shape” determines the subsequent transport and deposition of the droplets within an area around the mobile decontamination system. However, reaching and depositing droplets on surfaces also depends on specific geometries of objects forming these surfaces, as well as other objects located in the vicinity. For example, nearby objects may interfere with airflows directing dispersed decontaminant. Furthermore, access to some surfaces may be limited by other objects. Finally, additional objects in the area may present restrictions about using certain decontaminants, operating at certain environmental conditions (e.g., temperature, humidity, and the like). As such, the deposition from the fixed "plume shape" from the nozzle may be affected by the target geometry. Without additional controls, a fixed "plume shape" can cause non-uniform coverage of different surfaces with the decontaminant droplets. Some surfaces may receive excessive amounts of the decontaminant (which may damage these surfaces), while other surfaces may receive insufficient amounts or not at all (and remain contaminated).

The mobile decontamination unit addresses this issue by determining aerosol dispersing parameters based on specific area characteristics, such as orientations of various surfaces. In some examples, relative orientations of different surfaces in the same area are considered due to potential cross-effect of these surfaces while decontaminating the area. For example, air flows generated within the area may be blocked and/or redirected by some surfaces. The mobile decontamination unit is self-adjustable and reconfigurable. The mobile decontamination unit is also operable to control dispersing angles, dispersing amounts, droplet sizes, airflows carrying the droplets, temperature, and the like. The mobile decontamination unit is also movable within an operating area.

FIG. 1A is a schematic representation of mobile decontamination unit 300 deployed within area 100, which is represented as an aircraft cabin. Aircraft cabins are highly-populated enclosed areas, which can be contaminated. Furthermore, aircraft cabins have many different surfaces 110 made from different materials making decontamination process particularly challenging. Yet, decontamination of aircraft cabins has to be performed in a fast and efficient manner, e.g., between flights without leaving undesirable chemical residues.

It should be noted that mobile decontamination unit 300 may be deployed together with another mobile decontamination unit 300 in the same area 100 as, for example, shown in FIG. 1A. Each mobile decontamination unit 300 may be responsible for decontaminating a portion of area 100. Referring to FIG. 1A, mobile decontamination unit 300 on the left may be responsible for decontaminating all seats in the left row and a left portion of the center row. Mobile decontamination unit 300 on the right may be responsible for decontaminating all seats in the right row and a right portion of the center row as, for example, schematically shown in an expanded view in FIG. 1B. Each mobile decontamination unit 300 may be movable along its respective aisle in this example. Alternatively, each mobile decontamination unit 300 may be used decontaminate entire area 100 but using different aerosol dispersing parameters. For example, different types of decontaminants may be used by each mobile decontamination unit 300. Operation of each mobile decontamination unit 300 may be synchronized with other units.

Figure 1B:
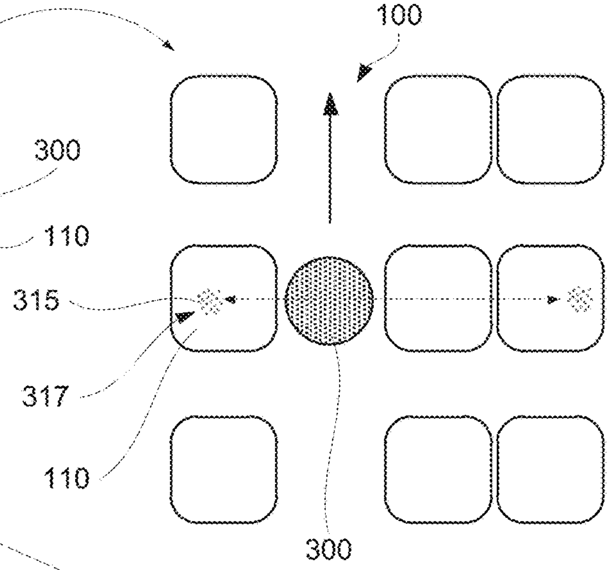
Figure 1C:
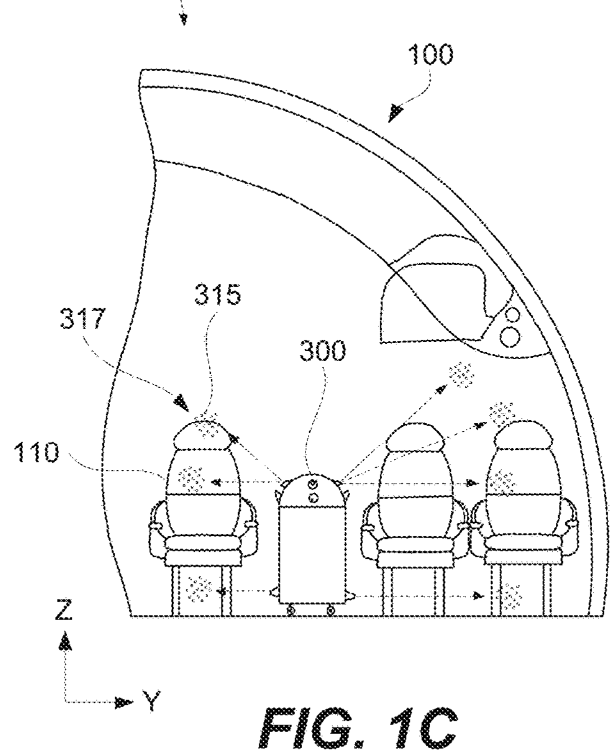

Mobile decontamination unit 300 is operable to disperse decontaminant 315 in an aerosol form as decontaminant droplets 317. In some examples, mobile decontamination unit 300 is operable to disperse decontaminant 315 in different directions at the same time, as schematically shown in FIGS. 1B and 1C. For example, mobile decontamination unit 300 may be operable to disperse decontaminant 315 to the seat on the right and both seats on the left of mobile decontamination unit 300. It should be noted that in the example shown in FIGS. 1B and 1C, mobile decontamination unit 300 is positioned at different distances to different seats (e.g., the leftmost seat being the farthest from mobile decontamination unit 300) that are being decontaminated. Furthermore, mobile decontamination unit 300 in this example disperses decontaminant 315 to only one seat on the right and two seats on the left. The control of dispersing angles, dispersing amounts, droplet sizes, airflows carrying the droplets, temperature, and other like parameters allows to decontaminate all seats in a uniform manner.

Referring to FIG. 1C, mobile decontamination unit 300 may also decontaminate different portions of area 100 in the vertical direction (along the Z axis). For example, mobile decontamination unit 300 is shown to decontaminate areas under the seats, around the seats, and over the seats. In some examples, mobile decontamination unit 300 may be raise its head portion containing nozzle to access and decontaminate even higher portions of area 100 as, for example, shown in FIG. 1D.

While the following description references an aircraft, it should be appreciated that the subject matter described herein may be applicable to any types of vehicles, objects, or areas. For example, the subject matter described herein could just as readily be applied to decontaminate an automotive vehicle, a building, and/or any other area that is at least potentially contaminated. Accordingly, any reference to the "aircraft" throughout the following description is merely meant to illustrate one potential application of the teachings of the subject matter described herein.

As used herein, the term "decontaminating" refers to removing, inactivating, and/or destroying a pathogen on a surface and/or item such that the pathogen is no longer capable of transmitting infectious particles and such that the surface and/or item is rendered safe for handling, use, and/or disposal. The term "pathogen" refers to any disease, illness, and/or infection-producing agent including, without limitation, a germ, a virus, a bacterium, a protozoon, a fungus, and/or a microorganism.

As used herein, an element or step recited in the singular and proceeded with the word "a" or "an" should be understood as not excluding plural elements or steps unless such exclusion is explicitly recited. Furthermore, references to "one example" of the or the "exemplary example" are not intended to be interpreted as excluding the existence of additional examples that also incorporate the recited features.

Examples of Mobile Decontamination Units

Figure 2B:
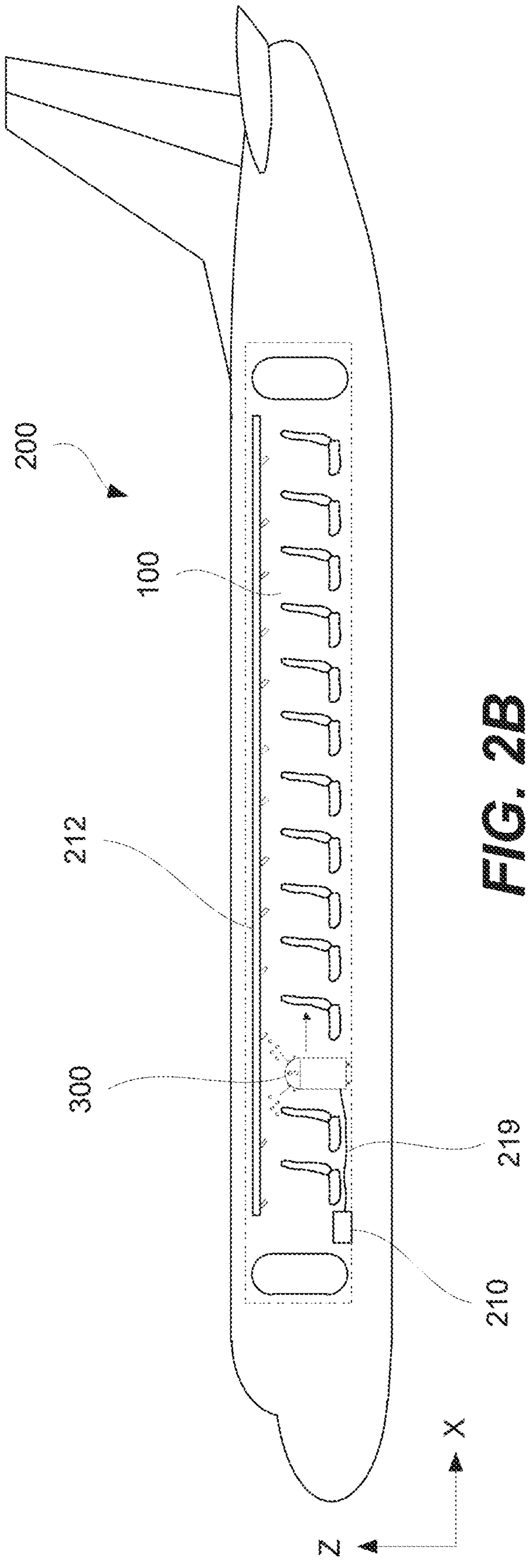
FIG. 2B is a schematic representation of a mobile decontamination unit operably coupled to a remote unit of the area, in accordance with some examples.

Description of mobile decontamination unit 300 and system 200, which mobile decontamination unit 300 may be a part of, will be first presented, before describing methods of using mobile decontamination unit 300. FIG. 2A is a schematic block diagram of mobile decontamination unit 300. As shown in FIG. 2A, mobile decontamination unit 300 may be a part of system 200, which may include other components, such as one or more remote units 210. Remote unit 210 may be also present in area 100. One example of remote unit 210 is heating-ventilation-air-conditioning (HVAC) unit 212 as, for example, schematically shown in FIG. 2B. Other examples include a humidifier, an ozone generator, a power supply, a decontaminant supply, a central controller, and the like. Remote units 210 should be distinguished from various components of mobile decontamination unit 300. In some examples, system 200 or at least is an environmental system of an aircraft. In these examples, area 100 is the interior of the aircraft Remote units 210 may be connected to mobile decontamination unit 300 using tether 219. It should be noted that tether 219 allows for mobile decontamination unit 300 to move within area 100 as, for example, schematically shown in FIG. 2B. This type of connection may be used to exchange information and control instructions, transmit power, transfer decontaminant 315, and the like. In some examples, remote unit 210 may be connected to mobile decontamination unit 300 wirelessly. This type of connection may be used to exchange information and control instructions, for example. In some examples, mobile decontamination unit 300 may not be permanently connected to remote unit 210 but temporary connection may be established when mobile decontamination unit 300 returns to abase (e.g., for recharging, transferring decontaminant 315). In some examples, mobile decontamination unit 300 operates as a standalone unit and is not part of system 200. In these examples, mobile decontamination unit 300 may have its own power source, decontaminant storage, unit controller, and/or other components enabling independent operation.

Figure 3A:
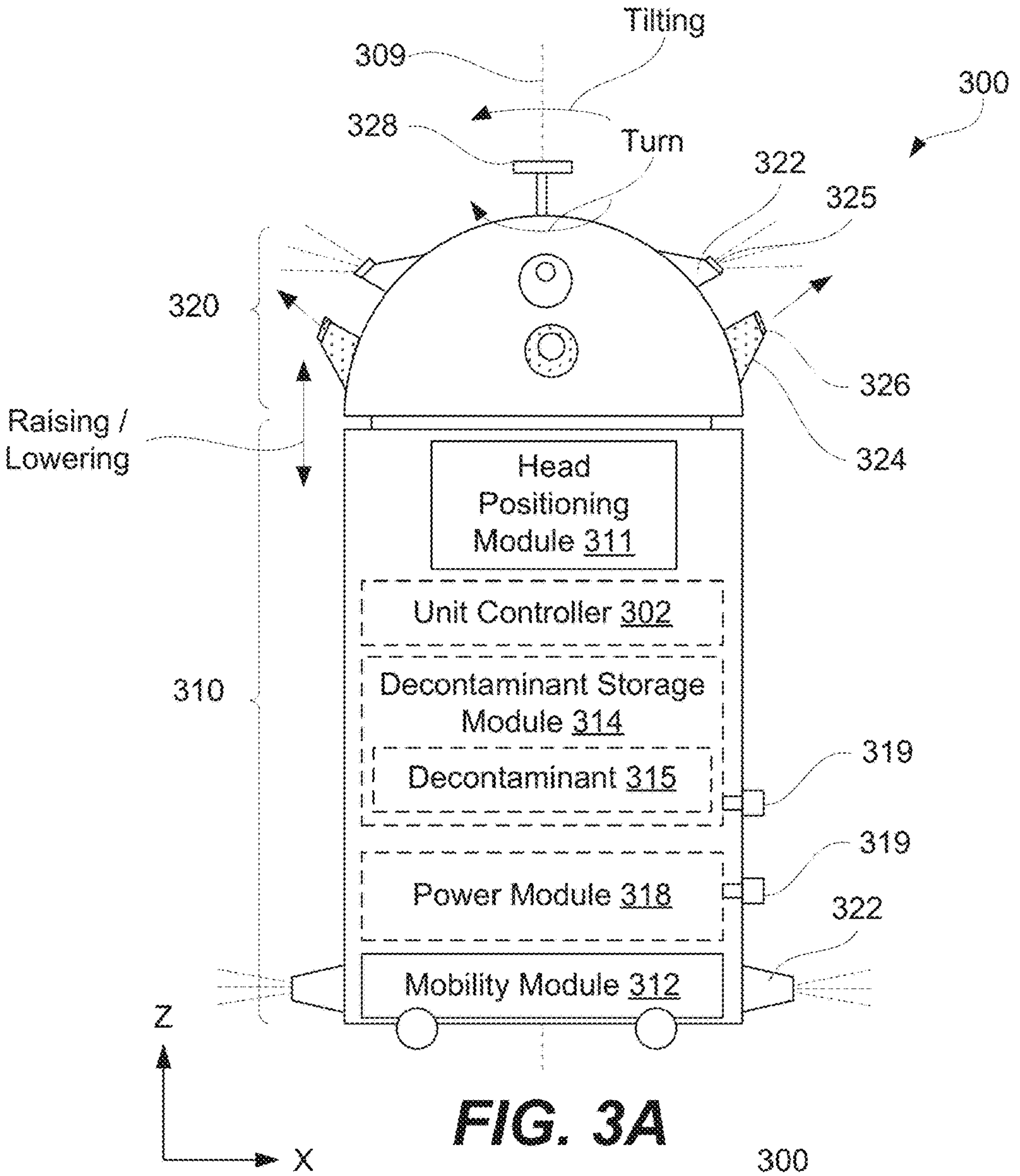
FIGS. 3A-3B are schematic representations of a mobile decontamination unit, in accordance with some examples.
Figure 3B:
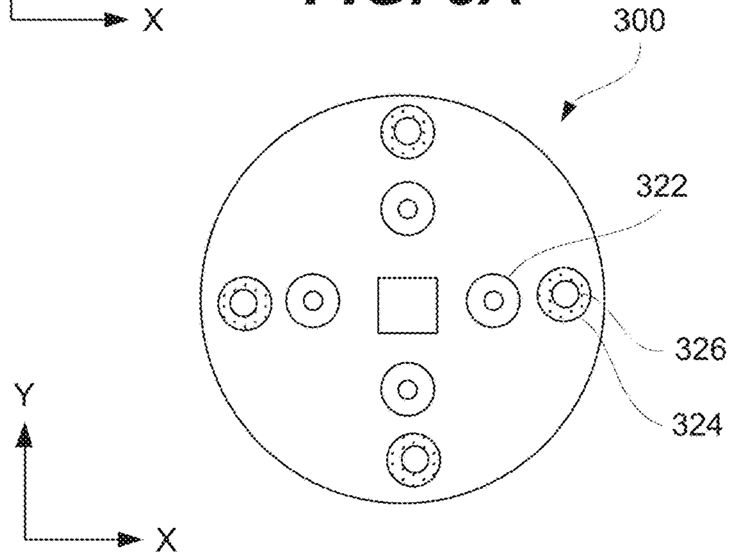

FIGS. 3A-3B are schematic representations of mobile decontamination unit 300, in accordance with some examples. Mobile decontamination unit 300 may comprise base portion 310 and head portion 320. Head portion 320 may be movably coupled to base portion 310. For example, head portion 320 may be raised relative to base portion 310 and/or rotate relative to base portion 310, e.g., rotate around center axis 309 of mobile decontamination unit 300. Furthermore, head portion 320 may be able to tilt relative to base portion 310 and relative to center axis 309. The movement of head portion 320 relative to base portion 310 may be provided by head positioning system 311 of mobile decontamination unit 300. Mobility of head portion 320 relative to base portion 310 may be utilized for distribution of decontaminant 315 in a particular manner (e.g., more uniformly) as further described below. Specifically, head portion 320 may support various components of mobile decontamination unit 300 operable to dispersed decontaminant 315 and direct decontaminant 315 to surfaces 110. Therefore, movement and orientation of head portion 320 relative to base portion 310 (and relative to area 100) may be utilized for decontaminant distribution as further described below.

Mobile decontamination unit 300 or, more specifically, base portion 310 may comprise mobility module 312 operable to move mobile decontamination unit 300 around area 100. Some mobility aspects are described above with reference FIG. 1A. For example, mobile decontamination unit 300 move along aisles of an aircraft cabin.

Mobile decontamination unit 300 or at least base portion 310 may have a cylindrical shape. This shape allows for mobile decontamination unit 300 move in area 100 and contact objects within area 100 without getting stuck on objects in the space.

Mobile decontamination unit 300 comprises at least one aerosol dispersing nozzle 322 and at least one aerosol directing fan 324. While this description refers to aerosol directing fan 324, one having ordinary skill in the art would recognize that other types of devices operable to direct decontaminant droplets 317 may be used, such as turbines, compressed air jets, and the like. For example, FIGS. 3A and 3B illustrate four aerosol dispersing nozzles 322 and four aerosol directing fans 324 positioned on head portion 320 of mobile decontamination unit 300. Additional aerosol dispersing nozzles 322 are shown on base portion 310 (e.g., to dispense decontaminant under the seats in an aircraft cabin). Each aerosol dispersing nozzle 322 is operable to disperse decontaminant 315 within area 100. Specifically, decontaminant 315 is dispersed in an aerosol form comprising decontaminant droplets 317 as, for example, schematically shown in FIGS. 1B and 1C. Aerosol directing fan 324 is operable to direct 450 decontaminant droplets 317 of decontaminant 315 to surfaces 110 in area 100.

In some examples, aerosol dispersing nozzle 322 and/or aerosol directing fan 324 is movable at least with respect to base portion 310. Aerosol dispersing nozzle 322 and aerosol directing fan 324 may be each independently movable relatively to base portion 310. Alternatively, aerosol dispersing nozzle 322 and aerosol directing fan 324 may be moved together as a set. For example, aerosol dispersing nozzle 322 and aerosol directing fan 324 may positioned on head portion 320 as shown in FIGS. 3A and 3B. Movement of head portion 320 relative to base portion 310 (and relative to area 100) will also cause aerosol dispersing nozzle 322 and aerosol directing fan 324 to move relative to base portion 310 (and relative to area 100). In this example, head portion 320 is used as a device orienting aerosol dispersing nozzle 322 and aerosol directing fan 324 in area 100, for example, to reach certain surfaces 110. It should be noted that the orientation of head portion 320 relative to base portion 310 may be changed, e.g., in order to change the orientation of aerosol dispersing nozzle 322 and aerosol directing fan 324 in area 100 and access new surfaces 110.

Independent movement of aerosol dispersing nozzle 322 and aerosol directing fan 324 provide processing flexibility. For example, changing the angle of an airflow generated by aerosol directing fan 324 relative to the plume of decontaminant droplets 317 generated by aerosol dispersing nozzle 322 will direct this plume to different surfaces 110. On other hand, moving aerosol dispersing nozzle 322 and aerosol directing fan 324 together (as a set) allows preserving their orientation and allow for simpler controls, especially when mobile decontamination unit 300 is equipped with multiple sets of aerosol dispersing nozzles 322 and aerosol directing fans 324. In some examples, all of these sets is moved together.

In some examples, aerosol dispersing nozzle 322 and/or aerosol directing fan 324 changes its orientation relative to head portion 320. Aerosol dispersing nozzle 322 and aerosol directing fan 324 may change their orientation independently or together, e.g., as a set. For example, one or both of aerosol dispersing nozzle 322 and aerosol directing fan 324 may be operable to tilt (independently or together) relative to head portion 320 and relative to center axis 309. In this example, head portion 320 may have a dome shape to support this tilting feature thereby allowing wider tilting angles (e.g., 90° on each side or even 180°). Furthermore, the dome shape of head portion 320 assists with air flow around head portion 320 and prevents accumulation of decontaminant 315 (after its dispersal) on or around head portion 320.

In some examples, aerosol directing fan 324 is equipped with heaters 326. Heater 326 is used to increase the temperature of area 100 or, more specifically, to increase the temperature of the air directed by fan 324. For example, efficacy of certain decontaminants depends on temperature. Furthermore, increasing temperature allows expediting decontamination process, supply less decontaminant, evaporate decontaminant residue from surfaces 110, and other purposes.

In some examples, aerosol dispersing nozzle 322 is equipped with electrostatic charging devices 325 operable to apply an electrostatic charge to decontaminant 315 at the time of the dispersion. Specifically, decontaminant droplets 317 are electrostatically charged, which may cause decontaminant droplets 317 to adhere more rapidly to surfaces 110. As a result, the amount of time needed for decontamination may be reduced and the decontamination process may go faster and potentially with less decontaminant being dispersed.

In some examples, mobile decontamination unit 300 comprises connector 319 operable to connect mobile decontamination unit 300, for example, to remote unit 210. As described above with reference to FIGS. 2A and 2B, tether 219 is used for such connections. During operation, tether 219 is connected to connector 319 and used for supplying electrical power, compressed air, and/or decontaminant 315. In some examples, tether 219 may be used transfer data and/or perform other like operations.

In some examples, mobile decontamination unit 300 comprises decontaminant storage module 314 operable to store decontaminant 315 onboard of mobile decontamination unit 300. This feature eliminates a need for tether, in some examples, and make mobile decontamination unit 300 more maneuverable in area 100.

In some examples, mobile decontamination unit 300 comprises a compressor for pressurizing decontaminant 216 onboard of mobile decontamination unit 300. Specifically, the compressor is operable to supply a pressure sufficient for distribution of decontaminant 315 through nozzle 322.

In some examples, mobile decontamination unit 300 comprises sensor 328. Some examples include, but are not limited to, as biological sensor 328*a*, chemical sensor 328*b*, temperature sensor 328*c*, humidity sensor 328*d*, camera 328*e*, and the like. Sensor 328 is operable to obtain area characteristics 102. In some examples, biological sensor 328*a* includes a bio-recognition component and a bio-transducer component. The recognition component, such as a bio-receptor, may use biomolecules to interact with the analyte of interest. This interaction may be measured by the bio-transducer, which outputs a measurable signal proportional to the presence of the target analyte in the sample. Some examples of chemical sensor 328*b* include a catalytic bead sensor, chemical field-effect transistor, electrochemical gas sensor, infrared point sensor, and ion-selective electrode. Examples of temperature sensor 328*c* include an infrared thermometer, resistance thermometer, thermistor, and thermocouple. A hygrometer or a humistor may be used for humidity sensor 328*d*.

In some examples, mobile decontamination unit 300 comprises unit controller 302 as, for example, schematically shown in FIGS. 2A and 3A. Alternatively, mobile decontamination unit 300 receives all control instructions from a remote unit and may not have its own unit controller 302. Unit controller 302, when present, is operable to determine aerosol dispersing parameters 305 based on area characteristics 102. Furthermore, unit controller 302 is operable to control operations of various other components of mobile decontamination unit 300, such as aerosol dispersing nozzle 322, aerosol directing fan 324, and mobility module 312. Mobile decontamination unit 300 may also include communication module 306 and/or database 304, which may be parts of unit controller 302 or standalone devices.

Unit controller 302 may be used to implement one or more computers and may include a processor unit, communications framework, memory, persistent storage, communications module, input/output (I/O) unit, and display. The communications framework may take the form of a bus system. The processor unit may serve to execute instructions for software that may be loaded into the memory. The processor unit may be a number of processors, a multi-processor core, or some other type of processor, depending on the particular implementation. The memory and persistent storage are examples of storage devices, which may be hardware units operable to store information, such as, for example, without limitation, data, program code in functional form, and/or other suitable information either on a temporary basis and/or a permanent basis. The memory, in these examples, may be, for example, a random access memory or any other suitable volatile or non-volatile storage device. The persistent storage may be a hard drive, a flash memory, a rewritable optical disk, a rewritable magnetic tape, or some combination of the above. In some examples, database 304 (which may include area characteristics 102) is stored in the persistent storage. The input/output unit of unit controller 302 may be used for input and output of data with other devices. For example, the input/output unit may provide a connection for user input through a keyboard, a mouse, and/or some other suitable input device.

Instructions for mobile decontamination unit 300 or, more specifically, unit controller 302, such as its operating system, applications, and/or programs may be located in the storage devices, which are in communication with the processor unit through the communications framework. The processes of the different examples may be performed by the processor unit using computer-implemented instructions, which may be located in a memory, such as the memory. These instructions are referred to as program code, computer usable program code, or computer readable program code that may be read and executed by a processor in the processor unit. The program code in the different embodiments may be embodied on different physical or computer readable storage media, such as the memory or persistent storage. The program code may be located in a functional form on the computer readable media that is selectively removable and may be loaded onto or transferred to unit controller 302 for execution by the processor unit. In these illustrative examples, the computer readable storage media is a physical or tangible storage device used to the store program code rather than a medium that propagates or transmits the program code.

Alternatively, the program code may be transferred to unit controller 302 using the computer readable signal media. The computer readable signal media may be, for example, a propagated data signal containing program code. For example, the computer readable signal media may be an electromagnetic signal, an optical signal, and/or any other suitable type of signal. These signals may be transmitted over communications links, such as wireless communications links, optical fiber cable, coaxial cable, a wire, and/or any other suitable type of communications link.

Figure 3C:
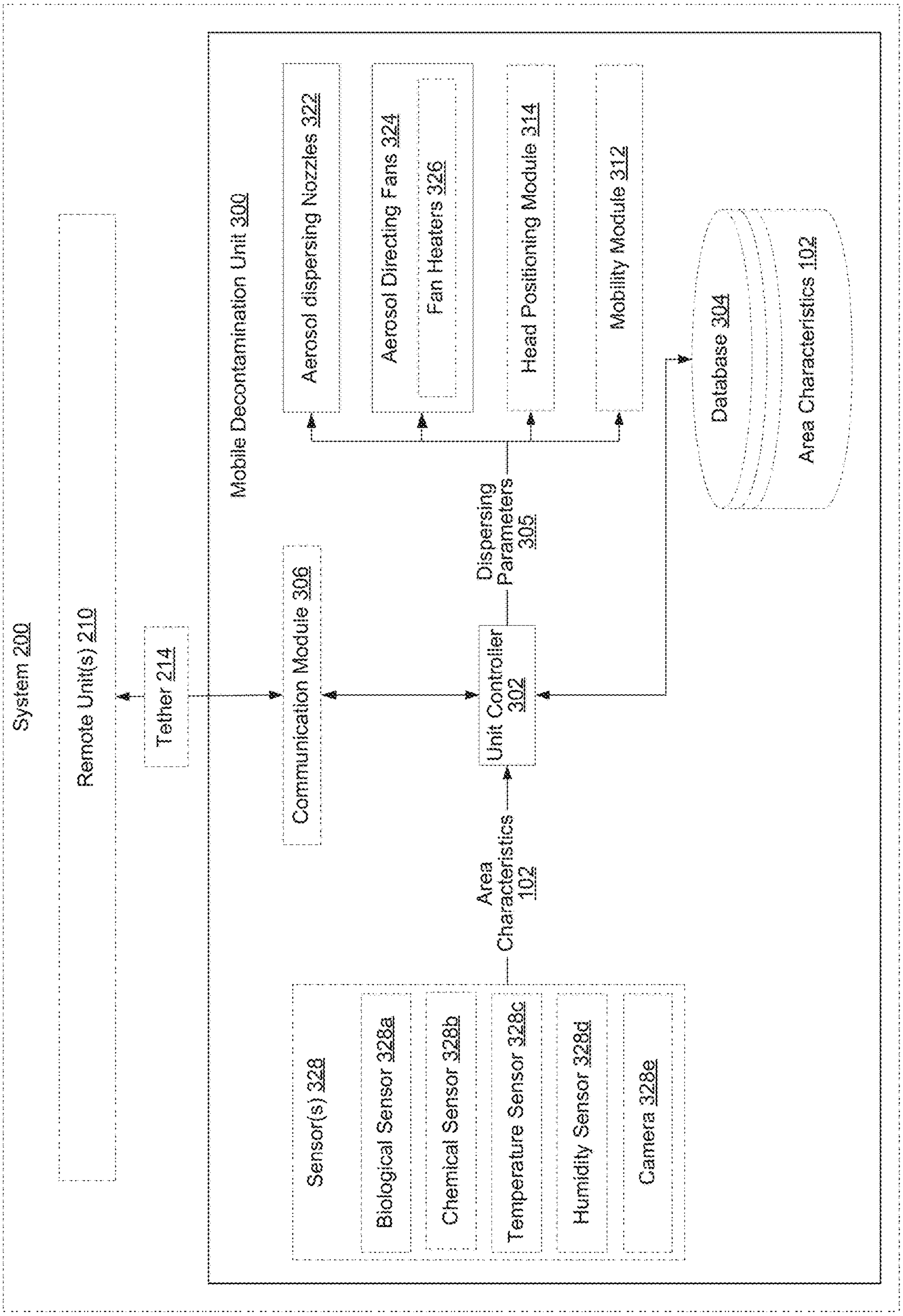
FIG. 3C is a schematic representation of information flows between various components of a mobile decontamination unit, in accordance with some examples.

FIG. 3C is a schematic representation of information flowing among various components of mobile decontamination unit 300, in accordance with some examples. The input components, such as sensor 328, provide information to unit controller 302 that includes area characteristics 102. For example, biological sensor 328*a* and chemical sensor 328*b* may be used for detection of contaminants within area 100 and provide information (area characteristics 102) about the detected contaminants to unit controller 302. Temperature sensor 328*c* and humidity sensor 328*d* may be used to measure temperature and humidity, respectively, inside area 100. Camera 328*e* may capture images of area 100 to determine orientations of different surfaces 110 within area and/or relative to mobile decontamination unit 300.

In some examples, unit controller 302 receives information from communication module 306 and/or database 304. In these examples, database 304 is used to store at least a portion of one or more characteristics of area 100 shown as area information in FIG. 2C. In other words, at least a portion of area characteristics 102 are stored locally at mobile decontamination unit 300. One example of such characteristics is area layout. Additional characteristics can be transmitted to mobile decontamination unit 300 and/or obtained by mobile decontamination unit 300. Communication module 306 is used to exchange information (area characteristics 102 and/or dispersing parameters 305) with other units, e.g., Remote Units 210 and/or other mobile decontamination units 300.

In some examples, unit controller 302 is integrated with communication module 306 and/or database 304 into one computer system. Various examples and features of computer systems are described below with reference to FIG. 7.

Once unit controller 302 determines dispensing parameters 305, these parameters are used to control various components of mobile decontamination unit 300, such as aerosol dispersing nozzle 322 and aerosol directing fan 324 as further described below.

Examples of Decontamination Methods

FIG. 4 is a process flowchart corresponding to method 400 for decontaminating of area 100, in accordance with some examples. Method 400 may comprise deploying mobile decontamination unit 300 in area 100, as schematically shown by block 410 in FIG. 4. In some examples, mobile decontamination unit 300 uses its own mobility module 312 for self-deployment in area 100 and without exposing any operators to potential contaminants in area 100, at least until the decontamination in completed. In some examples, mobile decontamination unit 300 is stored in a palletized container (PC) of an aircraft prior to its deployment. Alternatively, mobile decontamination unit 300 may be brought to the aircraft for decontamination.

Method 400 involves determining aerosol dispersing parameters 305 for mobile decontamination unit 300, as schematically shown by block 420 in FIG. 4. Aerosol dispersing parameters 305 are determined based on area characteristics 102. To achieve effective decontamination, various different area characteristics 102 are considered. Some examples of area characteristics 102 are humidity, temperature, contaminant type, orientation of surfaces 110 in area 100, and the like. In some examples, areas having different characteristics are decontaminated using different aerosol dispersing parameters. Furthermore, area characteristics 102 can be different from one part of area 100 to another. In some examples, smaller decontaminant droplets 317 and/or faster airflow is used to access remote surfaces of area (e.g., to prevent droplets 317 from settling before reaching these surfaces). When determining aerosol dispersing parameters 305, area characteristics 102 may be considered collectively. For example, a combination of humidity, temperature, and contaminant type is used for selection of decontaminant 315.

Determining aerosol dispersing parameters 305 during operation 420 may be also performed based on one or more characteristics of decontaminant 315 or, more specifically, selected decontaminant 315. Some examples of decontaminant characteristics include density, surface tension, composition, and the like. These characteristics typically impact distribution of decontaminant 315 in area 100. For example, switching from one type of decontaminant 315 to another one, effectively changes aerosol dispersing parameters 305. In this example, new aerosol dispersing parameters 305 are determined during operation 420.

In some examples, determining aerosol dispersing parameters 305 during operation 420 is performed using unit controller 302 of mobile decontamination unit 300. Furthermore, some or all aspect of operation 420 may be performed remotely from mobile decontamination unit 300 and transmitted (e.g., complete aerosol dispersing parameters 305) to mobile decontamination unit 300. For example, an initial set of aerosol dispersing parameters 305 may be transmitted to mobile decontamination unit 300 and then further modified at mobile decontamination unit 300 based on locally obtained characteristics 102 of area 100.

In some examples, determining aerosol dispersing parameters 305 during operation 420 comprises obtaining area characteristics 102, as schematically shown by block 422 in FIG. 4. Area characteristics 102 may be obtained using sensor 328 of mobile decontamination unit 300 or transmitted to mobile decontamination unit 300. Obtaining area characteristics 102 using sensor 328 allows deploying mobile decontamination unit 300 in area 100 and to achieve effective decontamination even when some information about area 100 is unknown. For example, temperature of area 100 may be initially unknown or it may change during decontamination. Yet, temperature has a significant impact on effectiveness of decontamination. In some examples, temperature is monitored locally by mobile decontamination unit 300 or, more specifically, a sensor of mobile decontamination unit 300. Another example of operation 422 is obtaining the orientation of surfaces 110 in area 100 using a camera of mobile decontamination unit 300 or from a database of mobile decontamination unit 300.

In some examples, presence of one or more contaminants in area 100 may be performed during operation 422. Some examples of contaminants include target pathogens and bio-agents, such as viruses, bacteria, prions, and funguses. The sensors may be configured to identify particular strains of the flu, the Ebola virus, tuberculosis, hemorrhagic fever, and/or any other contagion. In addition to the contaminants' presence, operation 422 may involve detecting concentrations and other characteristics of these contaminants. Operation 422 may be performed onboard of mobile decontamination unit 300 or some information may be transmitted to remote unit 210.

Operation 422 is optional and, in some examples, is not performed. In these examples, all characteristics 102 of area 100 necessary for operation of mobile decontamination unit 300 may be stored in mobile decontamination unit 300 (e.g., in database 304 of mobile decontamination unit 300) and/or transmitted to mobile decontamination unit 300 (e.g., from remote unit 210). For example, database 304 of mobile decontamination unit 300 may be preloaded with a layout of area, surface conditions, expected environmental conditions e.g., humidity, temperature. In some examples, some characteristics 102 are obtained mobile decontamination unit 300 after being deployed in area 100 (e.g., using sensor 328) while additional characteristics 102 are stored at mobile decontamination unit 300 and/or transmitted to mobile decontamination unit 300. Furthermore, all characteristics 102 may be obtained mobile decontamination unit 300 after being deployed in area 100 (e.g., using sensor 328). In other words, mobile decontamination unit 300 may have no information about area 100 at the time of deployment and no such information is transmitted to mobile decontamination unit 300 after its deployment.

In some examples, operation 420 comprises determining the orientation of aerosol dispersing nozzle 322 and/or the orientation of aerosol directing fan 324 based on the orientation of surfaces 110. This orientation relationship may be used to ensure that all surfaces 110 get adequate amounts of decontaminant 315 for effective decontamination. Furthermore, this orientation relationship ensures that surfaces (e.g., proximate to mobile decontamination unit 300) do not get excessive amounts of decontaminant 315, which may undesirably affect these surfaces.

In some examples, determining aerosol dispersing parameters 305 during operation 420 comprises changing one or more characteristics 102 of area 100, as schematically shown by block 424 in FIG. 4. For example, initially obtained characteristics 102 may be inadequate for effective decontamination. In a specific example, temperature of area 100 may be too low for decontaminant 315 to effectively react with and neutralize identified contaminants. These initially obtained characteristics 102 may be changed during operation 424. Returning to the temperature example above, the temperature of area 100 may be increased after deploying mobile decontamination unit 300 during operation 410 and prior to dispersing the decontaminant during operation 440. For example, aerosol dispersing parameters 305 may comprise a temperature ramping profile of the air directed by aerosol directing fan 324. The temperature ramping profile may be linear.

In some examples, operations shown in FIG. 4 may overlap. For example, changing characteristics during operation 424 may be performed while obtaining these characteristics during operation 422. Specifically, area characteristics 102 may be continuously monitored. If area characteristics 102 drift from one or more acceptable ranges, operation 424 may be performed to bring area characteristics 102 back into the acceptable ranges. Specifically, operation 424 may be performed while area characteristics 102 are being monitored resulting in overlap of operations 422 and 424. In this example, operation 422 may be used to provide control feedback to operation 424. In the same or other example, area characteristics 102 may need to be changed while dispersing decontaminant 315 during operation 440. For example, dispersing the decontaminant may lower the temperature of the environment (e.g., due to evaporation of decontaminant 315). In order to maintain effective decontamination, the temperature needs to be increased/area 100 needs to be heated. This heating (which is changing area characteristics 102 during operation 424) may be performed without stopping the dispersal of decontaminant 315 (assuming that the temperature is still within the acceptable range).

Figure 5A:
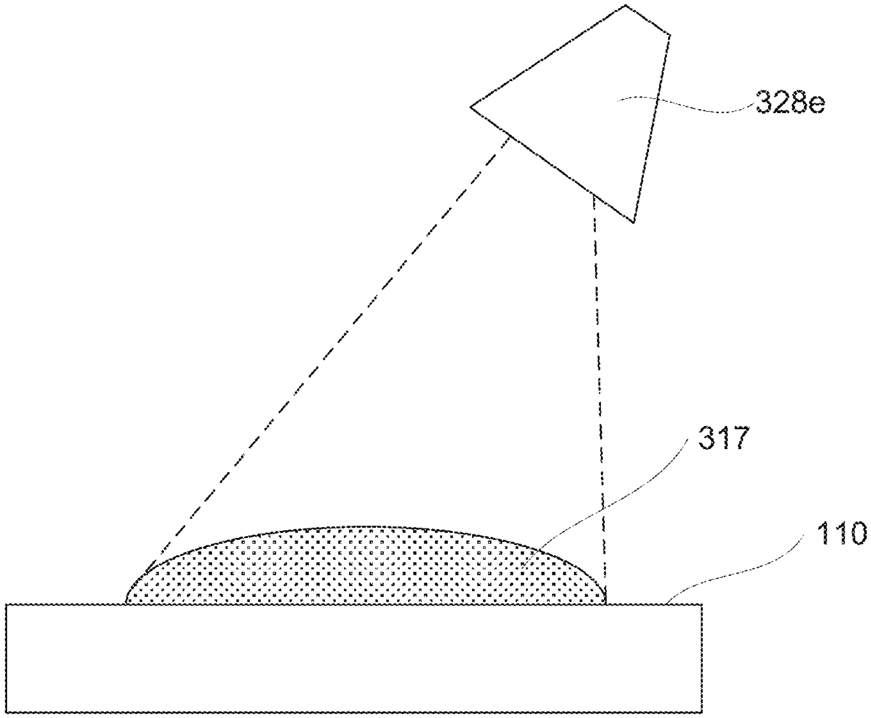
FIG. 5A is a schematic representation of a camera of a mobile decontamination unit capturing an image of a decontaminant droplet on a surface, in accordance with some examples.

In general, determining aerosol dispersing parameters during operation 420 (or, more specifically, obtaining these characteristics during operation 422) may be repeatedly or continuously performed while dispensing the decontaminant during operation 440. For example, the orientation of aerosol dispersing nozzle 322 and aerosol directing fan 324 may need to be reevaluated and, in some instances, changed while dispensing decontaminant 315. In another example, decontaminant droplets 317 may be observed on surfaces 110 using camera **328*e* as, for example, schematically shown in FIG. 5A. This observation of decontaminant droplets 317 on surfaces 110 may indicate about the coverage of surfaces with droplets 317 (e.g., sufficient or insufficient). Furthermore, this observation may be used as an indication of actual decontamination process. For example, decontamination may change hydrophobicity of surface 110 and decontaminant droplets 317 will have different shapes on surface 110** depending on the decontamination state.

Returning to changing one or more characteristics 102 during operation 424, these changes may be performed using one or more components of mobile decontamination unit 300. For example, aerosol directing fan 324 may be equipped with heaters 326, which may be used during operation 424 to increase the temperature of area 100. In the same or other examples, operation 424 comprises operating remote unit 210, as schematically shown with block 426 in FIG. 4. Remote unit 210 is external to mobile decontamination unit 300. Specifically, operation 426 may comprise sending control instructions from mobile decontamination unit 300 to remote unit 210. Remote unit 210 responds to these control instructions and perform its own operation to change one or more characteristics 102 of area 100.

Aerosol dispersing parameters 305 determined during operation 420 include at least one or more of identification of decontaminant 315 for dispensing in an aerosolized, temperature of air in area 100, humidity of air in area 100, relative timing of dispersing decontaminant 315 from aerosol dispersing nozzle 322 and flowing air from aerosol directing fan 324, duration of the dispersing, and the like. For example, aerosol dispersing parameters 305 may specify a relative humidity for the air in area 100 to be between about 40% and 80%, such as about 60%. As noted above, the aerosol dispersing parameters 305 may be different for different types of detected contaminants. Furthermore, the initial determined aerosol dispersing parameters 305 can be later changed.

Decontaminant 315 agent selected during operation 420 (as a part of aerosol dispersing parameters 305) may include one of more acids and/or one or more peroxides. For example, decontaminant 315 may include hydrogen peroxide. The concentration of hydrogen peroxide in decontaminant 315 may be less than 1% by weight and even less than 0.01% by weight. Hydrogen peroxide may be still effective at such low concentrations when combined with higher temperatures, such as between about 100 degrees Fahrenheit and 180 degrees Fahrenheit. In some examples, decontaminant 315 includes acetic acid. The concentration of the acetic acid may be may be less than 1% by weight and even less than 0.2% by weight.

In some examples, various pre-formulated decontaminants 315 may be used, such as STERIPLEX™ HC solution available from SBIOMED LLC in Orem, Utah. STERIPLEX™ HC solution includes 0.03% by weight of silver, 19% by weight of glycerol, 0.0004% by weight of sorbitol, 10% by weight of ethanol, 0.03% of hydrogen peroxide, 0.25% by weight of peroxyacetic acid, 0.19% by weight of acetic acid, and 70% by weight of water. STERIPLEX™ HC solution or other like solutions may be diluted with water to less than 50% by weight of the solution, less than 30% by weigh, and even less than 20% by weight. Decontaminant 315 may be supplied and, in some examples, formulated by mobile decontamination unit 300.

The temperature of the air in area 100 may be between about 100 degrees Fahrenheit and 180 degrees Fahrenheit or, more specifically, between about 120 degrees Fahrenheit and 140 degrees Fahrenheit. This temperature may be specifically selected to increase efficacy of decontaminant 315 with respect to the detected contaminants. Other considerations for selecting a particular temperature or, more generally, a particular temperature profile is to minimize duration of the heated air flowing through the aircraft compartment and to minimize a concentration of determined decontaminant 315.

Figure 5B:
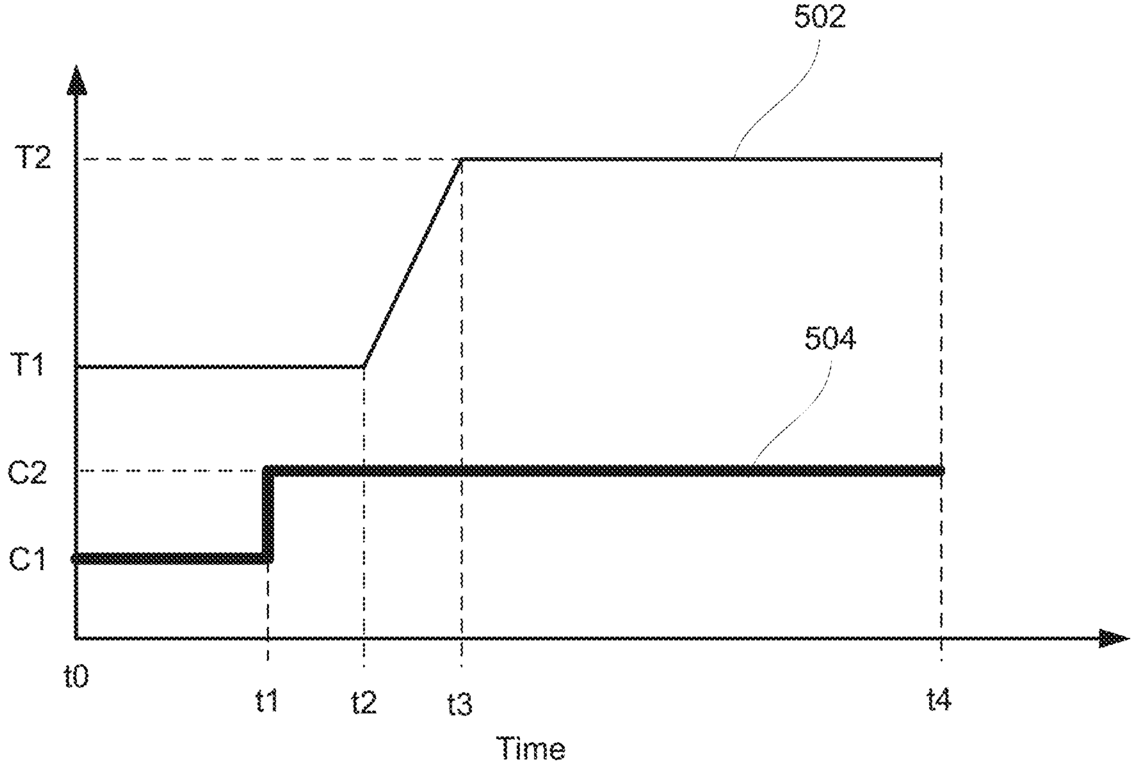
FIG. 5B is a schematic representation of a temperature profile and a concentration profile during a decontamination process, in accordance with some examples.

In some examples, temperature profile 502 may be changed during the decontamination process as for example shown in FIG. 5B. FIG. 5B also illustrates decontaminant concentration profile 504. In this situation, aerosol dispersing parameters 305 may include timing of the change and/or temperature ramping profile. In some examples, the temperature ramping profile is linear. For example, a lower initial temperature may be used to germinate spores, while a higher temperature may be later used together with the decontaminant 315 to kill the spores.

Method 400 may comprise changing aerosol dispersing parameters 305 of mobile decontamination unit 300, as schematically shown with block 430 in FIG. 4. For example, when the current configuration of mobile decontamination unit 300 is different from dispensing parameters determined during operation 420, mobile decontamination unit 300 may be reconfigured in accordance with the determined parameters. In other words, the current changing aerosol dispersing parameters 305 of mobile decontamination unit 300 are changed. In some examples, operation 420 may be repeated and new dispersing parameters 305 may be determined and may be different from the ones currently used by mobile decontamination unit 300. In this example, operation 430 is also performed. In some examples, operation 430 overlaps with operation 440, e.g., changing aerosol dispersing parameters 305 are performed while dispersing decontaminant 315.

Some examples of operation 430 include changing the orientation of aerosol dispersing nozzle 322 (relative to area 100), changing the orientation of aerosol directing fan 324 (relative to area 100), changing the power of heaters 326, changing the speed of aerosol directing fan 324, changing the dispensing rate of decontaminant 315, changing the dispensing conditions to achieve different droplet size, changing composition of decontaminant 315, and the like. For example, when mobile decontamination unit 300 completes decontamination of one portion of area 100, the orientations of aerosol dispersing nozzle 322 and, in some examples, the orientation of aerosol directing fan 324 may be changed (relative to area 100) to proceed with decontamination of another portion. Mobile decontamination unit 300 may maintain a certain relationship between the orientation of aerosol dispersing nozzle 322 and that of aerosol directing fan 324 since fan 324 is responsible for directing the aerosol dispersed from the nozzle to the surface being decontaminated. In some examples, this relationship (e.g., the relative orientation) of aerosol dispersing nozzle 322 and aerosol directing fan 324 is fixed. Aerosol directing fan 324 may be specifically directed at a plume of decontaminant droplets 317 created by aerosol dispersing nozzle 322. If the position of the plume relative to aerosol dispersing nozzle 322 does not change (e.g., no changes in decontaminant 315, flow rates of decontaminant 315 and air), then the relative orientation of aerosol dispersing nozzle 322 and aerosol directing fan 324 is maintained.

In some examples, the relative of aerosol dispersing nozzle 322 and aerosol directing fan 324 is changed. For example, the position of the plume of decontaminant droplets 317 relative to aerosol dispersing nozzle 322 may change and aerosol directing fan 324 may be need to be redirected to a new position of the plume. Furthermore, the aerosol directing fan 324 may be changed to direct the plume to a different location, e.g., a new surface.

Figure 1D:
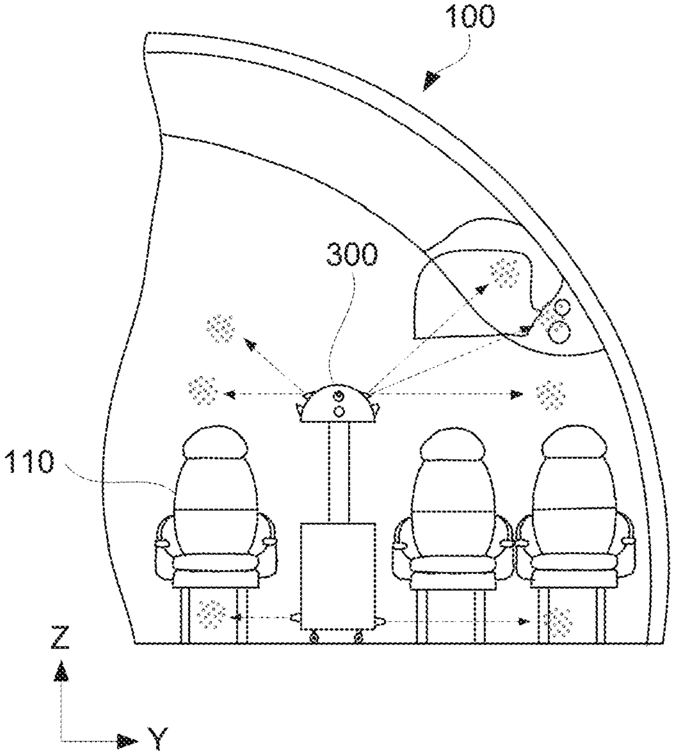

In some examples, changing the orientations of both aerosol dispersing nozzle 322 and aerosol directing fan 324 comprises changing the orientation of head portion 320 of mobile decontamination unit 300 relative to base portion 310. Specifically, head portion 320 may comprise (and support) aerosol dispersing nozzle 322 and aerosol directing fan 324. In other words, when head portion 320 changes its orientation relative to base portion 310 (and to area 100), it causes aerosol dispersing nozzle 322 and aerosol directing fan 324 to change their orientations relative to area 100 as well. For example, head portion 320 may be raised and/or rotated relative to base portion 310. As shown in FIGS. 1C and 1D, head portion 320 may be raised to access overhead compartments (e.g., stowage bins) in an aircraft. Furthermore, head portion 320 may be raised when decontaminant droplets 317 settle rapidly and/or when decontaminating remote surfaces (e.g., allowing for decontaminant droplets 317 to reach these surfaces before settling on more proximate surfaces).

In some examples, base portion 310 may also change its orientation relative to area 100, e.g., by moving mobile decontamination unit 300 in area 100 during operation 460 further described below. This may also cause aerosol dispersing nozzle 322 and aerosol directing fan 324 to change their orientations relative to area 100. As such, in some instances, operation 460 may be viewed as a subset of operation 430. However, movement of mobile decontamination unit 300 in area 100 may also be unrelated to aerosol dispersing parameters 305, e.g., to deploy or remove mobile decontamination unit 300 from area 100.

Method 400 may proceed with dispersing decontaminant 315 within area 100, as schematically shown by block 440 in FIG. 4. This operation may be performed in accordance with aerosol dispersing parameters 305. Decontaminant 315 is dispensed as a decontaminant droplets 317 using aerosol dispersing nozzle 322 of mobile decontamination unit 300.

Method 400 may proceed with directing decontaminant droplets 317 to surfaces 110 in area 100, as schematically shown by block 450 in FIG. 4. Aerosol directing fan 324 may be used for this operation by creating an airflow carrying decontaminant droplets 317. The airflow may be turbulent. Without being restricted to any particular theory, it is believed that a turbulent flow mitigated aerosol settling more effectively than, for example, a laminar flow. Aerosol directing fan 324 may be operable to generate a turbulent flow. Furthermore, aerosol directing fan 324 such that the airflow engages decontaminant droplets 317 soon after their dispensing, e.g., within 0.5 meters from aerosol dispersing nozzle 322 or even within 0.25 meters.

In some examples, operation 450 may also involve or at least account for any external airflows. The external airflows are the airflows that may be present in area 100, may be generated by remote units, but not generated by mobile decontamination unit 300. In other words, aerosol directing fan 324 do not contribute to external airflows. Yet, mobile decontamination unit 300 may utilize these external airflows, in addition to any airflows generated aerosol directing fan 324, to direct decontaminant droplets 317 to surfaces 110. The external airflows, if present in area 100, may be treated as a subset of area characteristics 102.

In some examples, directing decontaminant droplets 317 within area 100 during operation 450 involves changing some area characteristics 102. For example, directing decontaminant droplets 317 may change humidity, temperature, air flow, and other characteristics of area 100. As such, operation 424 may be viewed a subset of operation 450. Realizing that directing decontaminant droplets 317 within area 100 may change some area characteristics 102, obtaining area characteristics 102 during operation 422 may be performed repeatedly or even continuously to capture these changes in area characteristics 102 and, if necessary, changing area characteristics 102 back into desirable ranges or determining new aerosol dispensing parameters in response to the changes.

In some examples, dispersing decontaminant 315 within area 100 during operation 440 may overlap with directing decontaminant droplets 317 to surfaces 110 during operation 450. Specifically, aerosol directing fan 324 may operate at all times while dispersing decontaminant 315 is being dispensed by aerosol dispersing nozzle 322. In some examples, at least some dispersing of decontaminant 315 may be performed without aerosol directing fan 324 being operational. For example, decontamination of surfaces proximate to mobile decontamination unit 300 may be performed without operation 450. However, at least some surfaces in area 100 will benefit from operation 450 either because of their distance from mobile decontamination unit 300 or their position relative to the dispensing direction of aerosol dispersing nozzle 322.

Method 400 may further comprise moving mobile decontamination unit 300 in area 100, as schematically shown by block 460 in FIG. 4. This moving feature allows mobile decontamination unit 300 to decontaminate larger areas and/or to orientation its aerosol dispersing nozzle 322 and aerosol directing fan 324 relative to surfaces 110 in area 100. In some examples, moving mobile decontamination unit 300 in area 100 during operation 460 is performed while dispersing the decontaminant during operation 440.

Moving mobile decontamination unit 300 in area 100 during operation 460 may be performed automatically based on area characteristics 102. For example, mobile decontamination unit 300 may include a mobility module 312 that allows mobile decontamination unit 300 to move without external help e.g., from an operator. This feature allows to avoid exposing humans to potential contaminants and/or decontaminants in area 100.

In some examples, method 400 further comprises supplying compressed air, decontaminant, electrical power, and/or control instructions to mobile decontamination unit 300, as schematically shown by block 435 in FIG. 4. For example, decontaminant 315 may be supplied to mobile decontamination unit 300. More specifically, decontaminant 315 may be supplied while dispersing decontaminant 315 within area 100 during operation 440. This on-demand supply of decontaminant effectively reduces the weight of mobile decontamination unit 300 by eliminating a need for local storage. Decontaminant 315 may be supplied to mobile decontamination unit 300 using tether 219 extending within area 100. Tether 219 allows mobile decontamination unit 300 to move within area 100. In some examples, tether 219 may be use for supplying compressed air, power, and/or control instructions in addition to or instead of supplying decontaminant 315. In some examples, control instructions may be supplied to mobile decontamination unit 300 wirelessly (without tether 219).

When decontaminant 315 is not supplied on demand to mobile decontamination unit 300, decontaminant 315 may be stored in decontaminant storage module 314 onboard of mobile decontamination unit 300. Depending on the size of decontaminant storage module 314 and the amount of decontaminant 315 needed for area 100, mobile decontamination unit 300 may be operable to return to a refilling station where decontaminant 315 is added to decontaminant storage module 314.

CONCLUSION

Although the foregoing concepts have been described in some detail for purposes of clarity of understanding, after reading the above-disclosure it will be apparent that certain changes and modifications may be practiced within the scope of the appended claims. It should be noted that there are many alternative ways of implementing the processes, systems, and apparatuses. Accordingly, the present examples are to be considered as illustrative and not restrictive.

What is claimed is:

1. A mobile decontamination unit for decontaminating an area, the mobile decontamination unit comprising:

- a base portion, wherein the base portion comprises a mobility module configured to move the mobile decontamination unit;
- a head portion coupled to the base portion and configured to move relative to the base portion, the head portion comprising:
  - an aerosol dispersing nozzle configured to disperse a decontaminant within the area in an aerosol form, the aerosol form comprising decontaminant droplets; and
  - an aerosol directing fan configured to direct the decontaminant droplets dispersed by the aerosol dispersing nozzle; and
- a unit controller configured to:
  - determine aerosol dispersing parameters based on area characteristics; and
  - control operations of the aerosol dispersing nozzle, the aerosol directing fan, and/or the mobility module based on the aerosol dispersing parameters, wherein controlling operations includes changing orientation of the aerosol directing fan relative to the area, comprising changing orientation of the head portion of the mobile decontamination unit relative to the base portion of the mobile decontamination unit.

2. The mobile decontamination unit of claim 1, further comprising:

- a database, comprising at least a portion of the area characteristics.

3. The mobile decontamination unit of claim 1, further comprising:

- a sensor configured to obtain the area characteristics and transmit the area characteristics to the unit controller.

4. The mobile decontamination unit of claim 3, wherein the sensor is selected from the group consisting of a biological sensor, a chemical sensor, a temperature sensor, a humidity sensor, and a camera.

5. The mobile decontamination unit of claim 3, wherein the sensor is a biological sensor.

6. The mobile decontamination unit of claim 3, wherein the sensor is a chemical sensor.

7. The mobile decontamination unit of claim 3, wherein the sensor is a temperature sensor.

8. The mobile decontamination unit of claim 3, wherein the sensor is a humidity sensor.

9. The mobile decontamination unit of claim 1, wherein the unit controller is further configured to:

- control movement of the mobility module based on the area characteristics.

10. The mobile decontamination unit of claim 1, wherein the head portion further comprises a head body, wherein the aerosol dispersing nozzle and the aerosol directing fan are coupled to the head body, and wherein the aerosol dispersing nozzle and/or the aerosol directing fan are movable relative to the head body.

11. The mobile decontamination unit of claim 1, wherein the aerosol dispersing nozzle and the aerosol directing fan are pivotable and/or rotatable relative to a center axis of the mobile decontamination unit.

12. The mobile decontamination unit of claim 1, wherein the head portion is configured to raise, rotate, and/or tilt relative to the base portion.

13. The mobile decontamination unit of claim 3, wherein the sensor is a camera.

14. The mobile decontamination unit of claim 1, wherein the head portion further comprises a head body, wherein the aerosol dispersing nozzle and the aerosol directing fan are coupled to the head body, and wherein the aerosol dispersing nozzle is movable relative to the head body.

15. The mobile decontamination unit of claim 1, wherein the head portion further comprises a head body, wherein the aerosol dispersing nozzle and the aerosol directing fan are coupled to the head body, and wherein the aerosol directing fan is movable relative to the head body.

16. The mobile decontamination unit of claim 1, wherein the head portion is configured to raise relative to the base portion.

17. The mobile decontamination unit of claim 1, wherein the head portion is configured to rotate relative to the base portion.

18. The mobile decontamination unit of claim 1, wherein the head portion is configured to tilt relative to the base portion.

19. The mobile decontamination unit of claim 1, wherein the unit controller is configured to control operation of the aerosol dispersing nozzle.

20. The mobile decontamination unit of claim 1, wherein the unit controller is configured to control operation of the aerosol directing fan.

* * * * *